United States Patent
Marciniec et al.

(10) Patent No.: US 8,680,310 B2
(45) Date of Patent: Mar. 25, 2014

(54) (E)-STYRYL-ALKYNYLSUBSTITUTED SILICON COMPOUNDS AND METHOD OF OBTAINING (E)-STYRYL-ALKYNYLSUBSTITUTED SILICON COMPOUNDS

(75) Inventors: Bogdan Marciniec, Swarzedz (PL); Beata Dudziec, Poznan (PL); Monika Rzonsowska, Poznan (PL)

(73) Assignee: Adam Mickiewicz University, Poznan (PL)

( * ) Notice: Subject to any disclaimer, the term of this patent is extended or adjusted under 35 U.S.C. 154(b) by 0 days.

(21) Appl. No.: 13/395,196

(22) PCT Filed: Aug. 20, 2010

(86) PCT No.: PCT/PL2010/000076
§ 371 (c)(1), (2), (4) Date: Mar. 9, 2012

(87) PCT Pub. No.: WO2011/031171
PCT Pub. Date: Mar. 17, 2011

(65) Prior Publication Data
US 2012/0178955 A1 Jul. 12, 2012

(30) Foreign Application Priority Data
Sep. 11, 2009 (PL) .......................... 389012

(51) Int. Cl.
*C07F 7/02* (2006.01)
*C07F 7/04* (2006.01)

(52) U.S. Cl.
USPC .......................... 556/412; 556/431

(58) Field of Classification Search
None
See application file for complete search history.

(56) References Cited

PUBLICATIONS

Lyashenko et al., "α-Acetylene Hydrosilanes as Hydrosilylating Agents for Terminal Arylacetylenes," *Russian Journal of Organic Chemistry*, vol. 38, No. 2, pp. 147-149, 2002.
International Search Report issued in International Application No. PCT/PL2010/000076 dated Jan. 13, 2011.
International Preliminary Report on Patentability issued in International Application No. PCT/PL2010/000076 dated Mar. 13, 2012.

*Primary Examiner* — Nyeemah A Grazier
(74) *Attorney, Agent, or Firm* — Oliff PLC

(57) ABSTRACT

New (E)-styryl-alkynylsubstituted silicon compounds having the generalized formula 1 and A new method of obtaining (E)-styryl-alkynylsubstituted silicon compounds having the generalized formula 1.

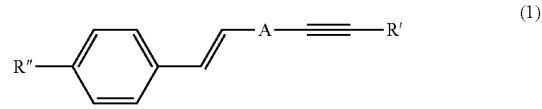

(1)

A denotes: phenylmethylsilyl, 1,4-bis(dimethylsilyl)benzene, 1,2-bis(dimethylsilyl)ethane, 1,1,3,3-tetramethyldisilazane, 1,1,3,3-tetramethyldisiloxane, R' denotes: tri(isopropyl)silyl, 1-pentyl, 2-(trimethylsiloxy)-2-butyl, 1-(trimethylsiloxy)-1-cyclohexyl, triethylgermyl, R' denotes: H or Cl and when A denotes phenylmethylsilyl then R" denotes also methyl or a methoxy group. A method of obtaining (E)-styrylalkynylsubstituted silicon compounds having the generalized formula 1 where A, R' and R" denote the same as stated above by way of a silylative coupling reaction between a suitable substituted styrene and a suitable vinylalkynylsubstituted silicon compound in the presence of a ruthenium(II) complex as catalyst.

18 Claims, No Drawings

(E)-STYRYL-ALKYNYLSUBSTITUTED SILICON COMPOUNDS AND METHOD OF OBTAINING (E)-STYRYL-ALKYNYLSUBSTITUTED SILICON COMPOUNDS

New (E)-styryl-alkynylsubstituted silicon compounds having the generalized formula 1 are the subject of the invention. The invention also relates to a new method of obtaining (E)-styryl-alkynylsubstituted silicon compounds having the generalized formula 1.

The essence of the invention are new, not previously known in the art, (E)-styryl-alkynylsubstituted silicon compounds having the generalized formula 1 where

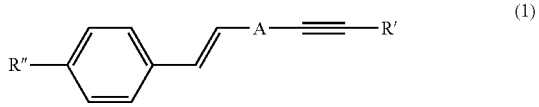

(1)

A denotes: phenylmethylsilyl, 1,4-bis(dimethylsilyl)benzene, 1,2-bis(dimethylsilyl)ethane, 1,1,3,3-tetramethyldisilazane, 1,1,3,3-tetramethyldisiloxane, R' denotes: tri(isopropyl)silyl, 1-pentyl, 2-(trimethylsiloxy)-2-butyl, 1-(trimethylsiloxy)-1-cyclohexyl, triethylgermyl, R" denotes: H or Cl and when A denotes phenylmethylsilyl then R" denotes also methyl or a methoxy group.

The new compounds, as disclosed in the patent, are high-boiling range, liquid, oily substances which are straw-coloured or yellow. The bifunctional (E)-styryl-alkynylsubstituted organosilicon compounds of the invention may be applied in organometallic synthesis as reactants for obtaining known, organic silicon compounds. The presence of a double and a triple bond enables the compounds to be potentially used as reactants in hydrometallation processes (e.g., hydrosilylation, hydroboronation etc.) which are applied in commercial process technologies. The silicon atom, incorporated between two π-coupled chromophore systems, facilitates photoinduced intramolecular charge transfer (CT), which has a direct effect on the respective interaction of the chromophores, while additional presence of silicon units influences the photo-physical properties of the compounds obtained, therefore, they are potentially useful as materials for optoelectronic applications.

In its second aspect, the invention relates to a method of obtaining (E)-styryl-alkynylsubstituted silicon compounds having the generalized formula 1 where A, R' and R" denote the same as stated above by way of a silylative coupling reaction between a suitable substituted styrene having the generalized formula 2 where

(2)

R" denotes the same as stated above, and a suitable vinyl-alkynylsubstituted silicon compound having the generalized formula 3 where

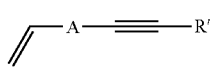

(3)

A and R' denote the same as stated above, in the presence of a ruthenium(II) complex as catalyst. The catalyst used is [carbonylchlorohydridebis(tricyclohexylphosphine)ruthenium(II)] or [carbonylchlorohydridebis(triphenylphosphine)ruthenium(II)] or [carbonylchlorohydridebis-(triisopropylphosphine)ruthenium(II)], in the amount of 0.5-3.5% mol relative to the vinyl-alkynylsubstituted silicon compound, preferably in the amount of 1-2%.

The reaction is carried out under inert gas and in a solvent selected from a group of aromatic organic compounds, most preferably toluene or benzene.

In the method of the invention, a mixture of a suitable vinyl-alkynylsubstituted silicon compound with a suitable styrene and catalyst is heated at a temperature not lower than 40° C. until completion of the reaction, and raw product is then refined. The reaction proceeds at any ratio of the reactants, although a lot of byproducts are formed in the case of unfavorable ratios. If equimolar quantities of styrene and the vinyl-alkynylsubstituted silicon compound are used, the selectivity of the process lowers and products of homocoupling of the vinyl-alkynylsubstituted silicon compound are observed in the post-reaction mixture in addition to the desirable product. Preferably, styrene or a suitable substituted styrene is used in an at least 1.2-fold excess relative to the vinyl-alkynylsubstituted silicon compound.

The reaction of the invention is carried out in the temperature range 40-90° C., preferably 80-90° C. Generally, the reaction time is 18-48 hrs, preferably 24 hrs.

The synthesis of the invention is carried out in a reactor which is protected from moisture, equipped with a reflux condenser, a mixing device and under inert gas, most preferably argon. The reactor is filled, in the following order, with: catalyst, solvent, vinyl-alkynylsubstituted silicon compound, and then styrene or substituted styrene. All of the liquid reactants as well as the solvent ought to be dewatered and deoxidized because of the sensitivity and decomposability of the catalyst in the presence of any traces of water and oxygen. The reaction mixture is then heated and mixed until the reaction is complete.

Reversing the order in which the reactants are introduced, i.e., first styrene or substituted styrene, then the vinyl-alkynylsubstituted silicon compound is also possible though it potentially reduces the selectivity of the process.

Raw product is separated and refined. Usually, separation consists of the evaporation of the solvent and any residual unreacted reactants from the post-reaction mixture, followed by purification of the raw product by removing the catalyst on a chromatographic column, filled with silica gel or silica modified with 15% $Et_3N$, using aliphatic hydrocarbons, preferably hexane or pentane, as eluent. Distillation at reduced pressures may be used as a variant of the separation and purification of the raw products although, in some cases, during the distillation process the decomposition of the products may occur due to their high boiling ranges.

In the second embodiment of the invention, the (E)-styryl-alkynylsubstituted silicon compounds are obtained as a result of conducting a "one-pot" reaction sequence in a single reactor, without separating the intermediate, i.e., the vinyl-alkynylsubstituted silicon compound.

The reaction sequence is a silylative coupling of terminal alkynes with divinylsubstituted silicon compounds, followed by a silylative coupling of the first-reaction products, i.e., the vinyl-alkynylsubstituted organosilicon compounds, with styrene or substituted styrene.

In the first step, the reaction is carried out between a divinylsubstituted silicon compound having the generalized formula 4 where

 (4)

A denotes the same as stated above, and the terminal alkyne having the generalized formula 5 where

 (5)

R' denotes the same as stated above.

In the first step, a mixture of a suitable divinylsubstituted silicon compound with a suitable alkyne and a catalyst is heated at a temperature not lower than 60° C. until completion of the reaction. The reaction proceeds at any ratio of the reactants, although a lot of byproducts are formed in the case of unfavorable ratios. If equimolar quantities of the alkyne and the divinylsubstituted silicon compound are used, the selectivity of the process lowers and alkyne dimerization products are observed in the post-reaction mixture in addition to the desirable reaction products. If a stoichiometric excess of divinylsilane is present in the system then the selectivity of the process shifts to favor the formation of the desirable reaction product, i.e., the vinyl-alkynylsubstituted silicon compound, while the alkyne dimerization reaction does not occur at all. If the excess of the vinylsubstituted silicon compound is too high, its homo-coupling reaction is favored, which has an adverse effect on the overall yield and selectivity of the process. The reaction of the invention is preferably effected at a 1.2 to 6-fold excess by mole of the vinylsubstituted silicon compound relative to the terminal alkyne.

On completion of the first step, the solvent, unreacted divinylorganic silicon compound and, possibly, the alkyne are removed by evaporation whereafter the temperature of the reaction mixture is reduced to temperature not higher than 90° C. Since the catalyst used in the first step is completely deactivated, it is necessary to add a Step 2 catalyst to catalyze the process of silylative coupling of the vinyl-alkynylsubstituted silicon compound with styrene or substituted styrene having the generalized formula 2 where R" denotes the same as stated above.

In the method of the invention, in the "one-pot" reaction sequence, the catalysts used in the first step are [carbonylchlorohydridebis(tricyclohexylphosphine)ruthenium(II)] or [carbonylchlorohydridebis(triisopropylphosphine)ruthenium(II)] while the catalysts used in the second step are [carbonylchlorohydridebis(tricyclohexylphosphine)ruthenium (II)] or [carbonylchlorohydridebis(tri phenylphosphine)ruthenium(II)] or [carbonylchlorohydridebis-(triisopropylphosphine)ruthenium (II)].

Both steps of the reaction are carried out under inert gas and in a solvent selected from a group of aromatic organic compounds, most preferably toluene for the first step and most preferably benzene for the second step, at temperatures not lower than 60° C. for the first step and not lower than 40° C. for the second step until completion of the reaction, whereafter raw product is refined.

The reaction of the invention is carried out at temperatures in the range 60-130° C. (preferably 120° C.) for Step 1 and 40-90° C. (preferably 80-90° C.) for Step 2.

The reaction time for Step 1 is, preferably, 24 hrs, and for Step 2 is 18-48 hrs, preferably 24 hrs.

In the second embodiment of the invention, the reactions are performed in a reactor which is protected from moisture, equipped with a reflux condenser, mixing device and under inert gas, most preferably argon. In the first step the reactor is filled, in the following order, with: catalyst for Step 1, solvent, divinylsubstituted silicon compound, and then the alkyne. All of the liquid reactants as well as the solvent ought to be dewatered and deoxidized because of the sensitivity and decomposability of the catalyst in the presence of any traces of water and oxygen. The reaction mixture is then heated and mixed until the reaction is complete. On completion of Step 1 the solvent and any unreacted divinylorganic silicon compound and, possibly, the alkyne, are evaporated, the temperature of the reaction mixture is reduced to temperatures not higher than 90° C., whereafter inert gas conditions are restored and the catalyst for Step 2, solvent, and a suitable styrene are introduced.

Raw product is separated and refined as in the first embodiment of the invention.

The subject of the invention is shown by way of examples, which are intended to illustrate rather than limit the scope of the invention.

The NMR data are listed in Table 1 while GCMS structural analysis data of the compounds obtained in the respective examples are shown in Table 2.

EXAMPLE I

A 10 mL reactor, equipped with a reflux condenser and mixing device, filled with an inert gas, 0.02 g of carbonylchlorohydridebis(tricyclohexylphosphine)ruthenium(II) was added and then, in the following order, 3.66 mL toluene, 0.90 g [(tri(isopropyl)silyl)ethynyl]methylphenylvinylsilane and 0.86 g styrene. The reaction mixture was heated at 90° C. for twenty four hours. Conversion of the vinyl-alkynylsubstituted organosilicon compound and raw product yield were 97%. In order to remove the catalyst from the system, the solvent and any residual unreacted reactants were evaporated from the post-reaction mixture, and the whole material was transferred onto a chromatographic column filled with silica gel, whereafter product was separated, using hexane as eluent. The product, [(tri(isopropyl)silyl)ethynyl]-methylphenyl-[(E)-styryl]silane, was obtained at a yield of 95% pure product in the form of an oily liquid, light yellow in color.

EXAMPLE II

As in reaction and purification conditions of Example I, to 2.75 mL of toluene the 0.02 g carbonylchlorohydridebis (triphenylphosphine)ruthenium(II) was added, and the reaction was carried out between 0.69 g [(tri(isopropyl)silyl)ethynyl]methylphenylvinylsilane and 0.87 g 4-chlorostyrene. Conversion of the vinyl-alkynylsubstituted organosilicon compound and raw product yield were 99%. The product, [(tri(isopropyl)silyl)ethynyl]-methylphenyl-[(E)-chlorostyryl]silane, was obtained at a yield of 95% pure product in the form of an oily liquid, light yellow in color.

EXAMPLE III

As in reaction and purification conditions of Example I, to 2.67 mL of toluene the 0.02 g chlorohydridecarbonylbis (triphenylphosphine)ruthenium(II) was added, and the reaction was carried out between 0.69 g [(tri(isopropyl)silyl)ethynyl]methylphenylvinylsilane and 0.74 g 4-methylstyrene.

Conversion of the vinyl-alkynylsubstituted organosilicon compound and raw product yield were 96%. The product, [(tri(isopropyl)silyl)ethynyl]-methylphenyl-[(E)-methylstyryl]silane, was obtained at a yield of 94% pure product in the form of an oily liquid, light yellow in color.

EXAMPLE IV

As in reaction and purification conditions of Example I, to 2.65 mL of toluene, the 0.02 g carbonylchlorohydridebis(triphenylphosphine)ruthenium(II) is added, and the reaction was carried out between 0.69 g [(tri(isopropyl)silyl)ethynyl]methylphenylvinylsilane and 0.86 g 4-methoxystyrene. Conversion of the vinyl-alkynylsubstituted organosilicon compound and raw product yield were 97%. The product, [(tri(isopropyl)silyl)ethynyl]-methylphenyl-[(E)-methoxystyryl]silane, was obtained at a yield of 93% pure product in the form of an oily liquid, light yellow in color.

EXAMPLE V

As in reaction and purification conditions of Example I, to 3.46 mL of toluene, the 0.02 g carbonylchlorohydridebis(tricyclohexylphosphine)ruthenium(II) was added, and the reaction was carried out between 1.11 g 1-{[(triethylgermyl)ethynyl]dimethylsilyl}-4-(dimethylvinylsilyl)-benzene and 0.86 g styrene. Conversion of the vinyl-alkynylsubstituted organosilicon compound and raw product yield were 98%. The product, 1-{[(triethylgermyl)ethynyl]dimethylsilyl}-4-{[(E)-styryl]dimethylsilyl}benzene, was obtained at a yield of 95% pure product in the form of an oily, yellow liquid.

EXAMPLE VI

As in reaction and purification conditions of Example I, to 3.41 mL of toluene the 0.02 g carbonylchlorohydridebis(tricyclohexylphosphine)ruthenium(II) was added, and the reaction was carried out between 1.11 g 1-{[triethylgermyl)ethynyl]dimethylsilyl}-4-(dimethylvinylsilyl)benzene and 1.15 g 4-chlorostyrene. Conversion of the vinyl-alkynylsubstituted organosilicon compound and raw product yield were 99%. The product, 1-{[(triethylgermyl)ethynyl]dimethylsilyl}-4-{[(E)-4-chlorostyryl]dimethylsilyl}benzene, was obtained at a yield of 96% pure product in the form of an oily liquid, light yellow in color.

EXAMPLE VII

As in reaction and purification conditions of Example I, to 3.70 mL of toluene, the 0.02 g carbonylchlorohydridebis(tricyclohexylphosphine)ruthenium(II) was added, and the reaction was carried out between 0.87 g 1-[(1-heptynyl)dimethylsilyl]-4-(dimethylvinylsilyl)benzene and 0.86 g styrene. Conversion of the vinyl-alkynylsubstituted organosilicon compound and raw product yield were 99%. The product, 1-[(1-heptynyl)dimethylsilyl]-4-{[(E)-styryl]dimethylsilyl}benzene, was obtained at a yield of 96% pure product in the form of an oily liquid, light yellow in color.

EXAMPLE VIII

As in reaction and purification conditions of Example I, to 3.65 mL of toluene, the 0.02 g carbonylchlorohydridebis(tricyclohexylphosphine)ruthenium(II) was added, and the reaction was carried out between 0.87 g 1-[(1-heptynyl)dimethylsilyl]-4-(dimethylvinylsilyl)benzene and 1.15 g 4-chlorostyrene. Conversion of the vinyl-alkynylsubstituted organosilicon compound and raw product yield were 99%. The product, 1-[(1-heptynyl)dimethylsilyl]-4-{[(E)-4-chlorostyryl]dimethylsilyl}benzene, was obtained at a yield of 97% pure product in the form of an oily liquid, light yellow in color.

EXAMPLE IX

As in reaction and purification conditions of Example I, to 3.67 mL of toluene, the 0.02 g carbonylchlorohydridebis(tricyclohexylphosphine)ruthenium(II) was added, and the reaction was carried out between 0.90 g 1-{[(cyclohexyl)ethynyl]dimethylsilyl}-4-(dimethylvinylsilyl)benzene and 0.86 g styrene. Conversion of the vinyl-alkynylsubstituted organosilicon compound and raw product yield were 99%. The product, 1-{[(cyclohexyl)ethynyl]dimethylsilyl}-4-{[(E)-styryl]dimethylsilyl}benzene, was obtained at a yield of 96% pure product in the form of an oily, yellow liquid.

EXAMPLE X

As in reaction and purification conditions of Example I, to 3.58 mL of toluene, the 0.02 g carbonylchlorohydridebis(tricyclohexylphosphine)ruthenium(II) was added, and the reaction was carried out between 0.98 g 1-{[(triethylgermyl)ethynyl]dimethylsilyl}-2-(dimethylvinylsilyl)ethane and 0.86 g styrene. Conversion of the vinyl-alkynylsubstituted organosilicon compound and raw product yield were 99%. The product, 1-{[(triethylgermyl)ethynyl]dimethylsilyl}-2-{[(E)-styryl]dimethylsilyl}ethane, was obtained at a yield of 93% pure product in the form of an oily liquid with a straw color.

EXAMPLE XI

As in reaction and purification conditions of Example I, to 3.54 mL of toluene, the 0.02 g carbonylchlorohydridebis(tricyclohexylphosphine)ruthenium(H) was added, and the reaction was carried out between 0.98 g 1-{[(triethylgermyl)ethynyl]dimethylsilyl}-2-(dimethylvinylsilyl )ethane and 0.86 g 4-chlorostyrene. Conversion of the vinyl-alkynylsubstituted organosilicon compound and raw product yield were 99%. The product, 1-{[(triethylgermyl)ethynyl]dimethylsilyl}-2-{[(E)-4-chlorostyryl]dimethylsilyl}ethane, was obtained at a yield of 94% pure product in the form of an oily, yellow liquid.

EXAMPLE XII

As in reaction conditions of Example I, to 3.56 mL of toluene, the of 0.02 g carbonylchlorohydridebis(tricyclohexylphosphine)ruthenium(II) was added, and the reaction was carried out between 1.01 g 1-{[(1-trimethylsiloxy-1-ethynyl)cyclohexyl]dimethylsilyl}-2-(dimethylvinylsilyl)ethane and 0.86 g styrene. Conversion of the vinyl-alkynylsubstituted organosilicon compound and raw product yield were 98%. In order to remove the catalyst from the system, the solvent and any residual unreacted reactants were evaporated from the post-reaction mixture and the whole material was transferred onto a chromatographic column filled with silica gel modified with a triethylamine, whereafter product was separated, using hexane as eluent. The product, 1-{[(1-trimethylsilyl-1-ethynyl)cyclohexyl]dimethylsilyl}-2-{[(E)-styryl]dimethylsilyl)-ethane, was obtained at a yield of 94% pure product in the form of an oily liquid, light yellow in color.

EXAMPLE XIII

As in reaction and purification conditions of Example XII, to 3.51 mL of toluene, the 0.02 g carbonylchlorohydridebis(tricyclohexylphosphine)ruthenium(II) was added, and the reaction was carried out between 1.01 g 1-{[(1-trimethylsiloxy-1-ethynyl)cyclohexyl]dimethylsilyl}-2-(dimethylvinylsilyl)ethane and 1.15 g 4-chlorostyrene. Conversion of the vinyl-alkynylsubstituted organosilicon compound and raw product yield were 99%. The product, 1-{[(1-trimethylsilyl-1-ethynyl)cyclohexyl]dimethylsilyl}-2-{[(E)-4-chlorostyryl]dimethylsilyl)ethane, was obtained at a yield of 95% pure product in the form of an oily, yellow liquid.

EXAMPLE XIV

As in reaction and purification conditions of Example XII, to 3.63 mL of toluene, the 0.02 g carbonylchlorohydridebis(tricyclohexylphosphine)ruthenium(II) was added, and the reaction was carried out between 0.94 g 1-{[3-methyl-3-(trimethylsiloxy)-1-pentynyl]dimethylsilyl}-2-(dimethylvinylsilyl)ethane and 0.86 g styrene. Conversion of the vinyl-alkynylsubstituted organosilicon compound and raw product yield were 99%. The product, 1-{[3-methyl-3-(trimethylsiloxy)-1-pentynyl]dimethylsilyl}-2-{[(E)-styryl]dimethylsilyl)ethane, was obtained at a yield of 95% pure product in the form of an oily liquid, light yellow in color.

EXAMPLE XV

As in reaction and purification conditions of Example XII, to 3.58 mL of toluene, the 0.02 g carbonylchlorohydridebis(tricyclohexylphosphine)ruthenium(II) was added, and the reaction was carried out between 0.94 g 1-{[3-methyl-3-(trimethylsiloxy)-1-pentynyl]dimethylsilyl}-2-(dimethylvinylsilyl)ethane and 1.15 g 4-chlorostyrene. Conversion of the vinyl-alkynylsubstituted organosilicon compound and raw product yield were 98%. The product, 1-{[3-methyl-3-(trimethylsiloxy)-1-pentynyl]dimethylsilyl}-2-{[(E)-4-chlorostyryl]-dimethylsilyl)ethane, was obtained at a yield of 95% pure product in the form of an oily, yellow liquid.

EXAMPLE XVI

As in reaction and purification conditions of Example XII, to 3.59 mL of toluene, the 0.02 g carbonylchlorohydridebis(tricyclohexylphosphine)ruthenium(II) was added, and the reaction was carried out between 0.97 g 1-[(1-trimethylsiloxy-1-ethynyl)cyclohexyl]-1,1,3,3-tetramethyl-3-vinyldisilazane and 0.86 g styrene. Conversion of the vinyl-alkynyl-substituted organosilicon compound and raw product yield were 95%. The product, 1-[(1-trimethylsiloxy-1-ethynyl)cyclohexyl]-1,1,3,3-tetramethyl-3-[(E)-styryl]disilazane, was obtained at a yield of 90% pure product in the form of an oily liquid, light yellow in color.

EXAMPLE XVII

As in reaction and purification conditions of Example XII, to 3.55 mL of toluene, the 0.02 g carbonylchlorohydridebis(tricyclohexylphosphine)ruthenium(II), and the reaction was carried out between 0.97 g 1-[(1-trimethylsiloxy-1-ethynyl)cyclohexyl]-1,1,3,3-tetramethyl-3-vinyldisilazane and 1.15 g 4-chlorostyrene. Conversion of the vinyl-alkynylsubstituted organosilicon compound and raw product yield were 97%. The product, 1-[(1-trimethylsiloxy-1-ethynycyclohexyl]-1,1,3,3-tetramethyl-3-[(E)-4-chlorostyryl]disilazane, was obtained at a yield of 90% pure product in the form of an oily, yellow liquid.

EXAMPLE XVIII

As in reaction and purification conditions of Example I, to 3.87 mL of toluene, the 0.02 g carbonylchlorohydridebis(tricyclohexylphosphine)ruthenium(II) was added, and the reaction was carried out between 0.70 g 1-(1-heptynyl)-1,1,3,3-tetramethyl-3-vinyldisiloxane and 0.86 g styrene. Conversion of the vinyl-alkynylsubstituted organosilicon compound and raw product yield were 98%. The product, 1-(1-heptynyl)-1,1,3,3-tetramethyl-3-[(E)-styryl]disiloxane, was obtained in the form of an oily liquid, light yellow in color.

EXAMPLE XIX

Step 1

A 10 mL reactor, equipped with a reflux condenser and mixing device, filled with an inert gas, a 0.02 g carbonylchlorohydridebis(tricyclohexylphosphine)ruthenium(II) was added and then, in the following order, with 2.12 mL toluene, 2.88 g phenylmethyldivinylsilane and 0.50 g ethynyltri(isopropyl)silane. The reaction mixture was heated at 120° C. for twenty four hours. On completion of the reaction the solvent was evaporated along with any unreacted methylphenyldivinylsilane and ethynyltri(isopropyl)silane, while the inactive Step-1 catalyst along with raw [(tri(isopropyl)silyl)ethynyl]methylphenylvinylsilane remained in the reactor.

Step 2

In the same reactor, a 0.01 g carbonylchlorohydridebis(tricyclohexylphosphine)ruthenium(II) was added and then, in the following order: 1.84 mL toluene and 0.43 g styrene, were added to a mixture of raw [(tri(isopropyl)silyl)ethynyl]methylphenylvinylsilane and the inactive Step-1 catalyst at a room temperature and under inert gas conditions. The reaction mixture was heated at 90° C. for twenty four hours. Product was separated under the purification conditions of Example I. The product, [(tri(isopropyl)silyl)ethynyl]-methylphenyl-[(E)-styryl]silane, was obtained with a total yield of 85% pure product, in the form of an oily liquid, light yellow in color.

EXAMPLE XX

Step 1

As in reaction conditions of Example XIX Step 1, to 2.12 mL of toluene, the 0.02 g carbonylchlorohydridebis(tricyclohexylphosphine)ruthenium(II) was added, and the reaction was carried out between 2.88 g methylphenyldivinylsilane and 0.50 g ethynyltri(isopropyl)silane. Raw [(tri(isopropyl)silyl)ethynyl]methylphenylvinylsilane was obtained.

Step 2

As in reaction conditions of Example XIX Step 2, to 1.90 mL of toluene, the 0.014 g carbonylchlorohydridebis(triphenylphosphine)ruthenium(II) was added, and the reaction was carried out between the [(tri(isopropyl)silyl)ethynyl]methylphenylvinylsilane obtained in Step 1 and 0.61 g 4-chlorostyrene. Product was separated under the purification conditions of Example I. The product, [(tri(isopropyl)silyl)ethynyl]-methylphenyl-[(E)-chlorostyryl]silane was obtained with a total yield of 86% pure product, in the form of an oily liquid, light yellow in color.

EXAMPLE XXI

Step 1

As in reaction conditions of Example XIX Step 1, to 3.29 mL of toluene, the 0.02 g carbonylchlorohydridebis(tricyclohexylphosphine)ruthenium(II) was added, and the reaction was carried out between 1.64 g 1,2-bis(dimethylvinylsilyl)ethane and 0.47 g 3-methyl-3-(trimethylsiloxy)pent-1-yne. Raw 1-{[3-methyl-3-(trimethylsiloxy)-1-pentynyl]dimethylsilyl}-2-(dimethylvinylsilyl)ethane was obtained.

Step 2

As in reaction conditions of Example XIX Step 2, to 1.84 mL of toluene, the 0.01 g carbonylchlorohydridebis(tricyclohexylphosphine)ruthenium(II) was added, and the reaction was carried out between the 1-{[3-methyl-3-(trimethylsiloxy)-1-pentynyl]dimethylsilyl}-2-(dimethylvinylsilyl)ethane obtained in Step 1 and 0.43 g styrene. Product was separated under the purification conditions of Example XII. The product, 1-{[3-methyl-3-(trimethylsiloxy)-1-pentynyl]dimethylsilyl}-2-{[(E)-styryl]dimethylsilyl)ethane was obtained with a total yield of 80% pure product in the form of an oily liquid, light yellow in color.

EXAMPLE XXII

Step 1

As in reaction conditions of Example XIX Step 1, to 3.29 mL of toluene, the 0.02 g carbonylchlorohydridebis(tricyclohexylphosphine)ruthenium(II) was added, and the reaction was carried out between 1.64 g 1,2-bis(dimethylvinylsilyl)ethane and 0.47 g 3-methyl-3-(trimethylsiloxy)pent-1-yne. Raw 1-{[3-methyl-3-(trim ethyl siloxy)-1-pentynyl]dimethylsilyl}-2-(dimethylvinylsilyl)ethane was obtained.

Step 2

As in reaction conditions of Example XIX Step 2, to 1.81 mL of toluene, the 0.01 g carbonylchlorohydridebis(tricyclohexylphosphine)ruthenium(II) was added, and the reaction was carried out between the 1-{[3-methyl-3-(trimethylsiloxy)-1-pentynyl]dimethylsilyl}-2-(dimethylvinylsilyl)ethane obtained in Step 1 and 0.57 g 4-chlorostyrene. Product was separated under the purification conditions of Example XII. The product, 1-{[3-methyl-3-(trimethylsiloxy)-1-pentynyl]dimethylsilyl}-2-{[(E)-4-chlorostyryl]dimethylsilyl)ethane, was obtained with a total yield of 82% pure product in the form of an oily, yellow liquid.

EXAMPLE XXIII

Step 1

As in reaction conditions of Example XIX Step 1, to 4.69 mL of toluene, the 0.02 g carbonylchlorohydridebis(triisopropylphosphine)ruthenium(II) was added, and the reaction was carried out between 2.29 g 1,1,3,3-tetramethyl-1,3-divinyldisilazane and 0.81 g 1-ethynyl-1-(trimethylsiloxy)cyclohexane. Raw 1-[(1-trimethylsiloxy-1-ethynyl)cyclohexyl]-1,1,3,3-tetramethyl-3-vinyldisilazane was obtained.

Step 2

As in reaction conditions of Example XIX Step 2, to 2.87 mL of toluene, the 0.016 g carbonylchlorohydridebis(tricyclohexylphosphine)ruthenium(II) was added, and the reaction was carried out between the 1-[(1-trimethylsiloxy-1-ethynyl)cyclohexyl]-1,1,3,3-tetramethyl-3-vinyldisilazane obtained in Step 1 and 0.69 g styrene. Product was separated under the purification conditions of Example XII. The product, 1-[(1-trimethylsiloxy-1-ethynyl)cyclohexyl]-1,1,3,3-tetramethyl-3-[(E)-styryl]disilazane, was obtained with a total yield of 85% pure product in the form of an oily liquid, light yellow in color.

EXAMPLE XXIV

Step 1

As in reaction conditions of Example XIX Step 1, to 4.69 mL of toluene, the 0.02 g carbonylchlorohydridebis(triisopropylphosphine)ruthenium(II) was added, and the reaction was carried out between 2.29 g 1,1,3,3-tetramethyl-1,3-divinyldisilazane and 0.81 g 1-ethynyl-1-(trimethylsiloxy)cyclohexane. Raw 1-[(1-trimethylsiloxy-1-ethynyl)cyclohexyl]-1,1,3,3-tetramethyl-3-vinyldisilazane was obtained.

Step 2

As in reaction conditions of Example XIX Step 2, to 2.84 mL of toluene, the 0.016 g carbonylchlorohydridebis(tricyclohexylphosphine)ruthenium(II) was added, and the reaction was carried out between the 1-[(1-trimethyl siloxy-1-ethynyl)cyclohexyl]-1,1,3,3-tetramethyl-3-vinyldisilazane obtained in Step 1 and 0.92 g 4-chlorostyrene. Product was separated under the purification conditions of Example XII. The product, 1-[(1-trimethylsiloxy-1-ethynyl)cyclohexyl]-1,1,3,3-tetramethyl-3-[(E)-4-chlorostyryl]disilazane, was obtained with a total yield of 86% pure product in the form of an oily, yellow liquid.

EXAMPLE XXV

Step 1

As in reaction conditions of Example XIX Step 1, to 6.25 mL of toluene, the 0.05 g carbonylchlorohydridebis(triisopropylphosphine)ruthenium(II) was added, and the reaction was carried out between 2.87 g 1,1,3,3-tetramethyl-1,3-divinyldisiloxane and 0.49 g 1-heptyne. Raw 1-(1-heptynyl)-1,1,3,3-tetramethyl-3-vinyldisiloxane was obtained.

Step 2

As in reaction conditions of Example XIX Step 2, to 2.48 mL of toluene, the 0.013 g carbonylchlorohydridebis(tricyclohexylphosphine)ruthenium(II) was added, and the reaction was carried out between the 1-(1-heptynyl)-1,1,3,3-tetramethyl-3-vinyldisiloxane obtained in Step 1 and 0.56 g styrene. Product was separated under the purification conditions of Example XII. The product, 1-(1-heptynyl)-1,1,3,3-tetramethyl-3-[(E)-styryl]disiloxane was obtained with a total yield of 85% pure product in the form of an oily liquid, light yellow in color.

TABLE 1

| Example | Compound | NMR analysis |
|---|---|---|
| I and XIX | [(tri(isopropyl)silyl)ethynyl]-methylphenyl-[(E)-styryl]silane | $^1$H NMR (CDCl$_3$) δ (ppm): 0.60 (s, CH$_3$Si); 1.08-1.19 (m, (CH$_3$)$_2$CH); 6.50-6.57 (d, J$_{H,H}$ = 19 Hz, 1H, (C$_6$H$_5$)HC=CHSi); 7.20-7.26 (d, J$_{H,H}$ = 19 Hz, 1H, (C$_6$H$_5$)HC=CHSi); 7.31-7.75 ((C$_6$H$_5$)HC=CHSi) $^{13}$C NMR (CDCl$_3$) δ (ppm): −1.88 (CH$_3$Si); 11.12 ((CH$_3$)$_2$CH); 18.63 ((CH$_3$)$_2$CH); 111.33, |

TABLE 1-continued

| Example | Compound | NMR analysis |
|---------|----------|--------------|
| | | 114.16 (C≡C); 123.86, 126.71, 127.86, 128.40, 128.53, 134.25 ($C_6H_5$); 129.50 (($C_6H_5$)CH=CHSi); 135.69, 137.92 ($c_i$-$C_6H_5$); 146.96 (($C_6H_5$)CH=CHSi) |
| II and XX | [(tri(isopropyl)silyl)ethynyl]-methylphenyl-[(E)-chlorostyryl]silane | $^1$H NMR (CDCl$_3$) δ (ppm): 0.59 (s, CH$_3$Si); 1.08-1.16 (m, (CH$_3$)$_2$CH); 6.46-6.52 (d, $J_{H,H}$ = 19 Hz, 1H, (4-Cl—$C_6H_4$)HC=CHSi); 7.12-7.18 (d, $J_{H,H}$ = 19 Hz, 1H, ((4-Cl—$C_6H_4$)HC=CHSi); ((4-Cl—$C_6H_5$)HC=CHSi); 7.27-7.76 (m, (4-Cl—$C_6H_4$), $C_6H_5$Si) $^{13}$C NMR (CDCl$_3$) δ (ppm): −1.95 (CH$_3$Si); 11.10 ((CH$_3$)$_2$CH); 18.62 ((CH$_3$)$_2$CH); 111.04, 114.43 (C≡C); 124.84, 127.41, 127.90, 128.69, 134.21 (4-Cl—$C_6H_4$, $C_6H_5$); 129.59 ((4-Cl—$C_6H_5$)CH=CHSi); 134.04, 135.40, 136.40 ($c_i$-(4-Cl—$C_6H_4$), $c_i$-$C_6H_5$); 145.50 ((4-Cl—$C_6H_4$)CH=CHSi) |
| III | [(tri(isopropyl)silyl)ethynyl]-methylphenyl-[(E)-4-methylstyryl]silane | $^1$H NMR (CDCl$_3$) δ (ppm): 0.57 (s, CH$_3$Si); 1.10-1.17 (m, (CH$_3$)$_2$CH); 2.36 (4-CH$_3$—$C_6H_4$); 6.42-6.45 (d, $J_{H,H}$ = 19 Hz, 1H, (4-CH$_3$—$C_6H_4$)HC=CHSi); 6.47-6.49 (d, $J_{H,H}$ = 19 Hz, 1H, (4-CH$_3$—$C_6H_4$)HC=CHSi)); 7.14-7.74 (m, (4-CH$_3$—$C_6H_4$), $C_6H_5$Si) $^{13}$C NMR (CDCl$_3$) δ (ppm): −1.8 (CH$_3$Si); 11.12 ((CH$_3$)$_2$CH); 18.63 ((CH$_3$)$_2$CH); 111.51, 113.99 (C≡C); 122.43, 126.64, 127.83, 129.22, 134.25 (4-Me—$C_6H_4$, $C_6H_5$); 129.44 ((4-Me—$C_6H_4$)CH=CHSi); 135.26, 135.87, 138.35 ($c_i$-(4-Me—$C_6H_4$), $c_i$-$C_6H_5$); 146.88 ((4-Me—$C_6H_4$)CH=CHSi) $^{29}$Si NMR (CDCl$_3$) δ (ppm): −2.2; −21.9 |
| IV | [(tri(isopropyl)silyl)ethynyl]-methylphenyl-[(E)-methoxystyryl]silane | $^1$H NMR (CDCl$_3$) δ (ppm): 0.59 (s, CH$_3$Si); 1.08-1.19 (m, (CH$_3$)$_2$CH); 6.34-6.40 (d, $J_{H,H}$ = 19 Hz, 1H, (4-OMe—$C_6H_4$)HC=CHSi); 7.15-7.21 (d, $J_{H,H}$ = 19 Hz, 1H, (4-OMe—$C_6H_4$)HC=CHSi); 6.88-6.91, 7.37-7.76 (m, 4-OMe—$C_6H_4$, $C_6H_5$) $^{13}$C NMR (CDCl$_3$) δ (ppm): 1.01 (CH$_3$Si); 11.11 ((CH$_3$)$_2$CH); 18.62 ((CH$_3$)$_2$CH); 111.53, 113.86 (C≡C); 120.85, 127.34, 127.81, 128.00, 134.23 (4-OMe—$C_6H_4$, $C_6H_5$); 129.41 ((4-Cl—$C_6H_5$)CH=CHSi); 135.96, 136.17, 159.86 ($c_i$-(4-OMe—$C_6H_4$), $c_i$-$C_6H_5$); 146.43 (4-OMe—$C_6H_4$)CH=CHSi) |
| V | 1-{[(triethylgermyl)ethynyl]-dimethylsilyl}-4-{[(E)-styryl]dimethylsilyl}benzene | $^1$H NMR (CDCl$_3$) δ (ppm): 0.46 (s, SiCH$_3$); 0.88-0.94 (qu, GeCH$_2$CH$_3$); 1.06-1.15 (tr, GeCH$_2$CH$_3$); 6.59-6.64 (d, $J_{H,H}$ = 20 Hz, 1H, HC=CHSi); 6.96-7.01 (d, $J_{H,H}$ = 19 Hz, 1H, HC=CHSi); 7.26-7.70 (m, $C_6H_5$; SiC$_6$H$_4$Si) $^{13}$C NMR (CDCl$_3$) δ (ppm): −0.54, 1.02 (SiCH$_3$); 5.89 (GeCH$_2$CH$_3$); 8.97 (GeCH$_2$CH$_3$), 111.48, 114.03 (C≡C); 126.48, 128.14, 128.50, 133.22, 133.27 ($C_6H_5$; SiC$_6$H$_4$Si); 120.00 (($C_6H_5$)CH=CHSi); 133.06, 138.15, 139.45 ($c_i$-$C_6H_5$, $c_i$-$C_6H_4$), 145.31 (($C_6H_5$)CH=CHSi) $^{29}$Si NMR (CDCl$_3$) δ (ppm): −21.90, −10.42 |
| VI | 1-{[(triethylgermyl)ethynyl]-dimethylsilyl}-4-{[(E)-4-chlorostyryl]dimethyl-silyl}benzene | $^1$H NMR (CDCl$_3$) δ (ppm): 0.46 (s, SiCH$_3$); 0.83-0.93 (qu, GeCH$_2$CH$_3$); 1.07-1.15 (tr, GeCH$_2$CH$_3$); 6.54-6.60 (d, $J_{H,H}$ = 20 Hz, 1H, (4-Cl—$C_6H_4$)HC=CHSi); 6.88-6.93 (d, $J_{H,H}$ = 19 Hz, 1H, ((4-Cl—$C_6H_4$)HC=CHSi); 7.29-7.70 (m, $C_6H_5$; SiC$_6$H$_4$Si) $^{13}$C NMR (CDCl$_3$) δ (ppm): −0.54, 1.02 (SiCH$_3$); 5.72 (GeCH$_2$CH$_3$); 8.97 (GeCH$_2$CH$_3$), 111.42, 114.07 (C≡C); 127.68, 128.66, 133.18, 133.27 ((4-Cl—$C_6H_4$), SiC$_6$H$_4$Si); 127.93 ((4-Cl—$C_6H_4$)CH=CHSi); 133.09, 133.79, 136.61, 139.28 ($c_i$-4-Cl—$C_6H_4$, $c_i$-$C_6H_4$), 143.89 (($C_6H_5$)CH=CHSi) $^{29}$Si NMR (CDCl$_3$) δ (ppm): −21.92, −10.33 |
| VII | 1-[(1-heptynyl)dimethylsilyl]-4-{[(E)-styryl]dimethylsilyl}-benzene | $^1$H NMR (CDCl$_3$) δ (ppm): 0.25-0.46 (s, SiCH$_3$); 0.92-2.30 (m, $C_5H_{11}$); 6.57-6.64 (d, $J_{H,H}$ = 20 Hz, 1H, HC=CHSi); 6.95-7.01 (d, $J_{H,H}$ = 19 Hz, 1H, HC=CHSi); 7.24-7.60 (m, $C_6H_4$; SiC$_6$H$_4$Si) $^{13}$C NMR (CDCl$_3$) δ (ppm): −2.60 (CH$_3$SiCH$_3$); 13.97-31.03 ($C_5H_{11}$); 82.08, 109.73 (C≡C); 126.48, 128.15, 128.50, 133.22, 133.27 ($C_6H_5$; SiC$_6$H$_4$Si); 126.99 (($C_6H_5$)CH=CHSi); 133.00, 138.14, 139.45 ($c_i$-$C_6H_5$, $c_i$-$C_6H_4$), 145.31 (($C_6H_5$)CH=CHSi) |

TABLE 1-continued

| Example | Compound | NMR analysis |
|---|---|---|
| VIII | 1-[(1-heptynyl)dimethylsilyl]-4-{[(E)-4-chlorostyryl]dimethylsilyl} benzene | $^1$H NMR (CDCl$_3$) δ (ppm): 0.38-0.47 (s, SiCH$_3$); 0.91-2.31 (m, C$_5$H$_{11}$); 6.54-6.60 (d, J$_{H,H}$ = 20 Hz, 1H, HC═CHSi); 6.88-6.94 (d, J$_{H,H}$ = 19 Hz, 1H, HC═CHSi); 7.31-7.61 (m, 4-Cl—C$_6$H$_4$; SiC$_6$H$_4$Si) $^{13}$C NMR (CDCl$_3$) δ (ppm): −2.87-(−2.51) (CH$_3$SiCH$_3$); 13.97-31.03 (C$_5$H$_{11}$); 82.05, 109.77 (C≡C); 127.68, 128.66, 133.21, 133.27 ((4-Cl—C$_6$H$_4$), SiC$_6$H$_4$Si) 127.94 ((4-Cl—C$_6$H$_4$)CH═CHSi); 133.04, 133.79, 136.60, 139.27 (c$_i$-4-Cl—C$_6$H$_4$, c$_i$-C$_6$H$_4$), 143.89 ((C$_6$H$_5$)CH═CHSi) |
| IX | 1-{[(cyclohexyl)ethynyl]dimethylsilyl}-4-{[(E)-styryl]dimethylsilyl}benzene | $^1$H NMR (CDCl$_3$) δ (ppm): 0.39-0.49 (m, SiCH$_3$); 1.29-2.55 (m, C$_6$H$_4$); 6.58-6.64 (d, J$_{H,H}$ = 20 Hz, 1H, HC═CHSi); 6.96-7.02 (d, J$_{H,H}$ = 19.5 Hz, 1H; HC═CHSi); 7.26-7.61 (m, C$_6$H$_5$; SiC$_6$H$_4$Si) $^{13}$C NMR (CDCl$_3$) δ (ppm): −2.61, −0.52 (CH$_3$SiCH$_3$); 24.76-32.53 (C$_6$H$_{11}$); 81.50, 113.80 (C≡C); 126.48, 128.14, 128.50, 133.22, 133.26 (C$_6$H$_5$; SiC$_6$H$_4$Si) 126.96 ((C$_6$H$_5$)CH═CHSi); 133.01, 138.11, 139.44 (c$_i$-C$_6$H$_5$, c$_i$-C$_6$H$_4$), 145.29 ((C$_6$H$_5$)CH═CHSi) |
| X | 1-{[(triethylgermyl)ethynyl]dimethylsilyl}-2-{[(E)-styryl]dimethylsilyl}ethane | $^1$H NMR (CDCl$_3$) δ (ppm): 0.14, 0.15 (s, SiCH$_3$); 0.51-0.67 (m, CH$_2$CH$_2$); 0.79-0.91 (qu, GeCH$_2$CH$_3$); 1.07-1.13 (tr, GeCH$_2$CH$_3$); 6.44-6.50 (d, J$_{H,H}$ = 20 Hz, 1H, HC═CHSi); 6.85-6.91 (d, J$_{H,H}$ = 20 Hz, 1H, HC═CHSi); 7.22-7.45 (m, (C$_6$H$_4$HC═CHSi) $^{13}$C NMR (CDCl$_3$) δ (ppm): −3.56, −2.06 (SiCH$_3$); 5.87 (GeCH$_2$CH$_3$); 7.83, 8.69 (CH$_2$CH$_2$); 8.96 (GeCH$_2$CH$_3$), 111.91, 113.42 (C≡C); 126.35, 127.91, 128.49 (C$_6$H$_5$); 128.38 ((C$_6$H$_5$)CH═CHSi); 138.42 (c$_i$, C$_6$H$_5$); 144.14 ((C$_6$H$_5$)CH═CHSi) |
| XI | 1-{[(triethylgermyl)ethynyl]dimethylsilyl}-2-{[(E)-4-chlorostyryl]dimethylsilyl}ethane | $^1$H NMR (CDCl$_3$) δ (ppm): 0.12, 0.14 (s, SiCH$_3$); 0.50-0.66 (m, CH$_2$CH$_2$); 0.79-0.87 (qu, GeCH$_2$CH$_3$); 1.06-1.12 (tr, GeCH$_2$CH$_3$); 6.41-6.46 (d, J$_{H,H}$ = 20 Hz, 1H, HC═CHSi); 6.79-6.84 (d, J$_{H,H}$ = 20 Hz, 1H, HC═CHSi); 7.27-7.37 (m, (4-Cl—C$_6$H$_4$)HC═CHSi) $^{13}$C NMR (CDCl$_3$) δ (ppm): −3.62, −2.06 (SiCH$_3$); 5.72 (GeCH$_2$CH$_3$); 7.71, 8.65 (CH$_2$CH$_2$); 8.94 (GeCH$_2$CH$_3$), 111.97, 113.34 (C≡C); 127.53, 128.62 (4-Cl—C$_6$H$_4$); 129.32 ((4-Cl—C$_6$H$_4$)CH═CHSi); 133.49, 136.89 (c$_i$, C$_6$H$_4$Cl); 142.80 ((4-Cl—C$_6$H$_4$)CH═CHSi) |
| XII | 1-{[(1-trimethylsilyl-1-ethynyl)-cyclohexyl]dimethylsilyl}-2-{[(E)-styryl]dimethylsilyl)ethane | $^1$H NMR (CDCl$_3$) δ (ppm): 0.05, 0.15 (s, CH$_3$Si); 0.19 (s, (CH$_3$)$_3$SiO); 0.51-0.62 (m, SiCH$_2$CH$_2$Si); 1.22-1.82 (m, (C$_6$H$_{10}$)C≡); 6.44, 6.50 (d, J$_{H,H}$ = 19 Hz, 1H, (C$_6$H$_5$)HC═CHSi); 6.87, 6.92 (d, J$_{H,H}$ = 19 Hz, 1H, (C$_6$H$_5$)HC═CHSi); 7.26-7.46 (C$_6$H$_5$) $^{13}$C NMR (CDCl$_3$) δ (ppm): −3.59, −2.33 (CH$_3$SiCH$_2$CH$_2$SiCH$_3$); 2.13 (CH$_3$SiO); 7.84, 8.46 (SiCH$_2$CH$_2$Si); 23.14-70.21 ((C$_6$H$_{10}$)C≡); 88.91, 110.41 (C≡C); 126.33, 127.94, 128.50 (C$_6$H$_5$); 128.18 ((C$_6$H$_5$)CH═CHSi); 138.34 (c$_i$, C$_6$H$_5$); 142.69 ((C$_6$H$_5$)CH═CHSi) |
| XIII | 1-{[(1-trimethylsilyl-1-ethynyl)-cyclohexyl]dimethylsilyl}-2-{[(E)-4-chloro-styryl]dimethylsilyl)ethane | $^1$H NMR (CDCl$_3$) δ (ppm): 0.03, 0.14 (s, CH$_3$Si); 0.18 (s, (CH$_3$)$_3$SiO); 0.51-0.61 (m, SiCH$_2$CH$_2$Si); 1.25-1.85 (m, (C$_6$H$_{10}$)C≡); 6.41, 6.67 (d, J$_{H,H}$ = 19 Hz, 1H, (4-Cl—C$_6$H$_4$)HC═CHSi); 6.79, 6.85 (d, J$_{H,H}$ = 19 Hz, 1H, (4-Cl—C$_6$H$_4$)HC═CHSi); 7.26-7.37 (4-Cl—C$_6$H$_4$) $^{13}$C NMR (CDCl$_3$) δ (ppm): −3.50, −2.18 (CH$_3$SiCH$_2$CH$_2$SiCH$_3$); 2.26 (CH$_3$SiO); 7.92, 8.57 (SiCH$_2$CH$_2$Si); 23.30-70.22 ((C$_6$H$_{10}$)C≡); 88.80, 110.45 (C≡C); 127.45, 128.55 (4-Cl—C$_6$H$_4$); 129.09 ((4-Cl—C$_6$H$_4$)CH═CHSi); 133.44, 136.75 (c$_i$, C$_6$H$_4$Cl); 142.69 ((4-Cl—C$_6$H$_4$)CH═CHSi) |
| XIV and XXI | 1-{[3-methyl-3-(trimethylsiloxy)-1-pentynyl]dimethylsilyl}-2-{[(E)-styryl]dimethylsilyl)ethane | $^1$H NMR (CDCl$_3$) δ (ppm): 0.13-0.15 (s, SiCH$_3$); 0.19 (s, OSiCH$_3$); 0.53-0.66 (m, SiCH$_2$CH$_2$Si); 0.96-0.99 (t, CH$_3$CH$_2$); 1.42 (s, CCH$_3$); 1.55-1.68 (m, CH$_2$CH$_3$); 6.45-6.50 (d, J$_{H,H}$ = 19 Hz, 1H, HC═CHSi); 6.87-6.92 (d, J$_{H,H}$ = 19 Hz, 1H, HC═CHSi); 7.24-7.46 (C$_6$H$_4$) $^{13}$C NMR (CDCl$_3$) δ (ppm): −3.60, −2.38 (CH$_3$Si); |

TABLE 1-continued

| Example | Compound | NMR analysis |
|---|---|---|
| | | 1.95 (s, OSiCH$_3$); 7.78-8.42 (SiCH$_2$CH$_2$Si); 9.04 (CH$_3$CH$_2$); 30.81 (CH$_3$C); 37.88 (CH$_3$CH$_2$); 70.17 (CH$_3$C); 87.66, 110.36 (C≡C; 126.34, 127.93, 128.50 (C$_6$H$_5$); 128.20 (C$_6$H$_5$HC=CHSi); 138.36 (c$_i$-C$_6$H$_5$); 144.20 (C$_6$H$_5$HC=CHSi); $^{29}$Si NMR (CDCl$_3$) δ (ppm): −14.48; −3.36; 13.26 |
| XV and XXII | 1-{[3-methyl-3-(trimethylsiloxy)-1-pentynyl]-dimethylsilyl}-2-{[(E)-4-chloro-styryl]dimethylsilyl}ethane | $^1$H NMR (CDCl$_3$) δ (ppm): 0.07, 0.14 (s, SiCH$_3$); 0.18 (s, OSiCH$_3$); 0.51-0.64 (m, SiCH$_2$CH$_2$Si); 0.87-0.99 (t, CH$_3$CH$_2$); 1.41 (s, CCH$_3$); 1.55-1.64 (m, CH$_2$CH$_3$); 6.41-6.46 (d, J$_{H,H}$ = 19 Hz, 1H, HC=CHSi); 6.80-6.85 (d, J$_{H,H}$ = 19 Hz, 1H, HC=CHSi); 7.28-7.37 (m, C$_6$H$_4$) $^{13}$C NMR (CDCl$_3$) δ (ppm): −3.65, −2.38 (CH$_3$Si); 1.95 (s, OSiCH$_3$); 7.73, 8.40 (SiCH$_2$CH$_2$Si); 9.03 (CH$_3$CH$_2$); 30.80 (CH$_3$C); 37.88 (CH$_3$CH$_2$); 70.17 (CH$_3$C); 87.59, 110.41 (C≡C); 127.54, 128.63 (4-Cl—C$_6$H$_4$); 129.18 ((4-Cl—C$_6$H$_4$)CH=CHSi); 133.54, 136.86 (c$_i$-4-Cl—C$_6$H$_4$); 142.81 ((4-Cl—C$_6$H$_4$)HC=CHSi) $^{29}$Si NMR (CDCl$_3$) δ (ppm): −14.44; −3.19; 13.29 |
| XVI and XXIII | 1-[(1-trimethylsiloxy-1-ethynyl)cyclohexyl]-1,1,3,3-tetramethyl-3-[(E)-styryl]-disilazane | $^1$H NMR (CDCl$_3$) δ (ppm): 0.07-0.86 (s, CH$_3$SiO; CH$_3$SiNHSiCH$_3$); 1.26-1.84 (m, (C$_6$H$_{10}$)C≡); 6.44, 6.51 (d, J$_{H,H}$ = 20 Hz, 1H, (C$_6$H$_5$)HC=CHSi); 6.90, 6.97 (d, J$_{H,H}$ = 20 Hz, 1H, (C$_6$H$_5$)HC=CHSi); 7.24-7.46 ((C$_6$H$_5$)HC=CHSi) $^{13}$C NMR (CDCl$_3$) δ (ppm): 0.89-2.26 (CH$_3$SiNHSiCH$_3$; CH$_3$SiO); 23.18-70.09 ((C$_6$H$_{10}$)C≡); 90.32, 108.88 (C≡C); 126.40; 128.38; 129.82 (C$_6$H$_5$); 127.92 ((C$_6$H$_5$)CH=CHSi); 138.23 (c$_i$-C$_6$H$_5$); 143.88 ((C$_6$H$_5$)CH=CHSi) |
| XVII and XXIV | 1-[(1-trimethylsiloxy-1-ethynyl)cyclohexyl]-1,1,3,3-tetramethyl-3-[(E)-4-chlorostyryl]disilazane | $^1$H NMR (CDCl$_3$) δ (ppm): 0.16-0.66 (s, CH$_3$SiO; CH$_3$SiNHSiCH$_3$); 1.23-1.84 (m, (C$_6$H$_{10}$)C≡); 6.43, 6.49 (d, J$_{H,H}$ = 19 Hz, 1H, (C$_6$H$_5$)HC=CHSi); 6.85, 6.91 (d, d$_{H,H}$ = 19 Hz, 1H, (C$_6$H$_5$)HC=CHSi); 7.24-7.39 ((4-Cl—C$_6$H$_4$)HC=CHSi) $^{13}$C NMR (CDCl$_3$) δ (ppm): 0.20-2.18 (CH$_3$SiNHSiCH$_3$; CH$_3$SiO); 23.17-70.09 ((C$_6$H$_{10}$)C≡); 90.22, 108.95 (C≡C); 127.56, 128.53 (4-Cl—C$_6$H$_4$); 130.75 ((4-Cl—C$_6$H$_4$)CH=CHSi); 133.51, 136.72 (c$_i$-C$_6$H$_4$Cl); 142.46 ((4-Cl—C$_6$H$_4$)CH=CHSi) |
| XVIII and XXV | 1-(1-heptynyl)-1,1,3,3-tetramethyl-3-[(E)-styryl]-disiloxane | $^1$H NMR (CDCl$_3$) δ (ppm): 0.24, 0.28 (s, SiCH$_3$); 0.87-2.24 (CH$_3$CH$_2$CH$_2$CH$_2$CH$_2$); 6.43-6.49 (d, J$_{H,H}$ = 19 Hz, 1H, (C$_6$H$_5$)HC=CHSi); 6.94-7.00 (d, J$_{H,H}$ = 19 Hz, 1H, (C$_6$H$_5$)HC=CHSi); 7.28-7.47 (m, C$_6$H$_5$) $^{13}$C NMR (CDCl$_3$) δ (ppm): 0.62, 2.53 (CH$_3$Si); 13.94-31.01 (C$_5$H$_{11}$); 84.26, 106.92 (C≡C); 126.51, 128.37, 128.47 (C$_6$H$_5$); 128.10 (C$_6$H$_5$HC=CHSi); 138.21 (c$_i$-C$_6$H$_5$); 144.28 (C$_6$H$_5$HC=CHSi) |

TABLE 2

| Example | Compound | GCMS analysis |
|---|---|---|
| I and XIX | [(tri(isopropyl)silyl)ethynyl]-methylphenyl-[(E)-styryl]silane | MS (EI) m/z (rel. int. %): 404 (3) [M$^+$], 389 (4) [M$^+$ − CH$_3$], 361 (100) [M$^+$ − C$_3$H$_7$)], 333 (14), 319 (80), 305 (16), 291 (17), 277 (19), 241 (18), 207 (22), 187 (15), 173 (12), 145 (44), 135 (35), 121 (21), 111 (18), 105 (19), 83 (21), 73 (14), 59 (11), 53 (11) |
| II and XX | [(tri(isopropyl)silyl)ethynyl]-methylphenyl-[(E)-chlorostyryl]silane | MS (EI) m/z (rel. int. %): 438 (5) [M$^+$], 395 (100) [M$^+$ − C$_3$H$_7$], 367 (43), 353 (76), 339 (15), 326 (14), 311 (21), 275 (21), 257 (13), 241 (20), 191 (14), 179 (32), 163 (20), 135 (54), 121 (35), 105 (26), 83 (29), 73 (25), 59 (20), 53 (16) |
| III | [(tri(isopropyl)silyl)ethynyl]-methylphenyl-[(E)-4-methylstyryl]silane | MS (EI) m/z (rel. int. %): 418 (8) [M$^+$], 403 (5) [M$^+$ − CH$_3$], 376 (100) [M$^+$ − CH$_3$H$_7$)], 348 (25), 334 (60), 292 (12), 256 (9), 222 (22), 187 (10), 159 (32), 145 (12), 135 (21), 121 (15), 105 (12), 73 (7) |

TABLE 2-continued

| Example | Compound | GCMS analysis |
|---|---|---|
| IV | [(tri(isopropyl)silyl)ethynyl]-methylphenyl-[(E)-methoxystyryl]silane | MS (EI) m/z (rel. int. %): 434 (19) [M$^+$], 391 (100) [M$^+$ – C$_3$H$_7$], 363 (14), 349 (35), 313 (15), 285 (13), 271 (13), 237 (18), 175 (26), 145 (10), 135 (22), 121 (17), 105 (12), 59 (12) |
| V | 1-{[(triethylgermyl)ethynyl]-dimethylsilyl}-4-{[(E)-styryl]dimethylsilyl}benzene | MS (EI) m/z (rel. int. %): 451 (100) [(M$^+$) – CH$_2$CH$_3$], 422 (47) [(M$^+$) – 2 × CH$_2$CH$_3$], 393 (18) [(M$^+$) – 3 × CH$_2$CH$_3$], 321 (8) [(M$^+$) – GeEt$_3$], 291 (8), 229 (6), 203 (11), 189 (7), 175 (6), 159 (6), 145 (35), 135 (11), 89 (6), 73 (11), 59 (9) |
| VI | 1-{[(triethylgermyl)ethynyl]-dimethylsilyl}-4-{[(E)-4-chlorostyryl]dimethyl-silyl}benzene | MS (EI) m/z (rel. int. %): 486 (100) [(M$^+$ + H) – CH$_2$CH$_3$], 458 (68) [(M$^+$ + H) – 2 × CH$_2$CH$_3$], 428 (44) [(M$^+$ + H) – 3 × CH$_2$CH$_3$], 401 (6), 356 (13) [(M$^+$ + H) – GeEt$_3$], 272 (8), 232 (11), 221 (10), 173 (10), 159 (10), 145 (10), 89 (11), 73 (17), 59 (13) |
| VII | 1-[(1-heptynyl)dimethylsilyl]-4-{[(E)-styryl]dimethylsilyl}-benzene | MS (EI) m/z (rel. int. %): 375 (24) [M$^+$ – CH$_3$], 361 (13), 325 (15), 298 (23), 238 (13), 219 (43), 161 (36), 145 (100), 119 (12), 73 (14), 59 (22) |
| VIII | 1-[(1-heptynyl)dimethylsilyl]-4-{[(E)-4-chlorostyryl]dimethyl-silyl} benzene | MS (EI) m/z (rel. int. %): 424 (3) [M$^+$], 409 (76) [M$^+$ – CH$_3$], 369 (20), 353 (50), 329 (12), 294 (14), 282 (100), 271 (58), 210 (30), 195 (18), 179 (18), 153 (52), 145 (22), 135 (27), 116 (12), 93 (28), 73 (45), 59 (63) |
| IX | 1-{[(cyclohexyl)ethynyl]dimethylsilyl}-4-{[(E)-styryl]-dimethylsilyl}benzene | MS (EI) m/z (rel. int. %): 402 (1) [M$^+$], 383 (18), 325 (10) [M$^+$ – C$_6$H$_5$)], 237 (20), 219 (100), 203 (11), 161 (23), 145 (68), 135 (18), 105 (10), 59 (17) |
| X | 1-{[(triethylgermyl)ethynyl]dimethylsilyl}-2-{[(E)-styryl]-dimethylsilyl}ethane | MS (EI) m/z (rel. int. %): 403 (17) [M$^+$ – CH$_2$CH$_3$], 375 (3), 285 (5), 271 (100), 243 (7), 227 (5), 185 (17), 161 (8), 145 (16), 135 (6), 105 (5), 73 (6), 59 (11) |
| XI | 1-{[(triethylgermyl)ethynyl]dimethylsilyl}-2-{[(E)-4-chloro-styryl]dimethylsilyl}ethane | MS (EI) m/z (rel. int. %): 452 [(M$^+$ + H) – CH$_3$], 428 (20), 398 (35), 371 (13), 354 (33), 294 (11), 268 (14), 159 (14), 133 (29), 101 (20), 73 (15), 59 (14) |
| XII | 1-{[(1-trimethylsilyl-1-ethynyl)-cyclohexyl]dimethylsilyl}-2-{[(E)-styryl]dimethyl-silyl)ethane | MS (EI) m/z (rel. int. %): 369 (6) [M$^+$ – SiC$_3$H$_9$], 269 (8), 233 (20), 171 (100), 161 (16), 145 (55), 135 (14), 73 (47), 59 (18) |
| XIII | 1-{[(1-trimethylsilyl-1-ethynyl)-cyclohexyl]dimethylsilyl}-2-{[(E)-4-chloro-styryl]dimethyl-silyl)ethane | MS (EI) m/z (rel. int. %): 403 (4) [M$^+$ – SiC$_3$H$_9$], 323 (9), 239 (13), 233 (21), 195 (9), 179 (14), 171 (100), 145 (18), 131 (9), 73 (52), 59 (17), 45 (18) |
| XIV and XXI | 1-{[3-methyl-3-(trimethylsiloxy)-1-pentynyl]-dimethylsilyl}-2-{[(E)-styryl]-dimethylsilyl)ethane | MS (EI) m/z (rel. int. %): 401 (1) [M$^+$ – CH$_3$], 387 (6), 297 (9), 233 (11), 213 (10), 161 (18), 145 (100), 135 (14), 117 (7), 73 (49), 59 (17), 45 911) |
| XV and XXII | 1-{[3-methyl-3-(trimethylsiloxy)-1-pentynyl]-dimethylsilyl}-2-{[(E)-4-chloro-styryl]dimethylsilyl)ethane | MS (EI) m/z (rel. int. %): 441 (1) [M$^+$ – CH$_3$], 421 (9) [M$^+$ – 2 × CH$_3$], 393 (6), 298 (6), 233 (12), 213 (10), 195 (18), 179 (22), 155 (12), 145 (100), 133 (12), 73 (79), 59 (26), 45 (20) |
| XVI and XXIII | 1-[(1-trimethylsiloxy-1-ethynyl)cyclohexyl]-1,1,3,3-tetramethyl-3-[(E)-styryl]-disilazane | MS (EI) m/z (rel. int. %): 414 (3) [M$^+$ – CH$_3$], 356 (12) [M$^+$ – SiC$_3$H$_9$)], 282 (40), 234 (18), 220 (100), 206 (27), 171 (30), 132 (46), 73 (89), 45 (25) |
| XVII and XXIV | 1-[(1-trimethylsiloxy-1-ethynyl)cyclohexyl]-1,1,3,3-tetramethyl-3-[(E)-4-chlorostyryl]disilazane | MS (EI) m/z (rel. int. %): 429 (2) [(M$^+$ + H) – Cl], 391 (8) [(M$^+$ + H) – SiC$_3$H$_9$)], 319 (14), 221 (100), 207 (24), 171 (21), 133 (23), 73 (95), 45 (22) |
| XVIII and XXV | 1-(1-heptynyl)-1,1,3,3-tetramethyl-3-[(E)-styryl]-disiloxane | MS (EI) m/z (rel. int. %): 330 (7) [M$^+$], 315 (10) [M$^+$ – CH$_3$], 301 (4) [M$^+$ – C$_2$H$_5$], 287 (6) [M$^+$ – C$_3$H$_7$], 273 (15) [M$^+$ – C$_4$H$_9$], 259 (6) [M$^+$ – C$_5$H$_{11}$], 245 (10), 235 (6), 227 (13), 219 (56), 209 (14), 193 (39), 133 (100), 117 (19), 73 (25), 59 (12) |

The invention claimed is:

1. An (E)-styryl-alkynylsubstituted silicon compound of having the generalized formula 1:

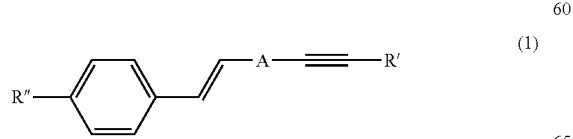

(1)

where:

A denotes: phenylmethylsilyl, 1,4-bis(dimethylsilyl)benzene, 1,2-bis(dimethylsilyl)-ethane, 1,1,3,3-tetramethyldisilazane, or 1,1,3,3-tetramethyldisiloxane;

R' denotes: tri(isopropyl)silyl, 1-pentyl, 2-(trimethylsiloxy)-2-butyl, 1-(trimethylsiloxy)-1-cyclohexyl, or triethylgermyl; and R" denotes: H or Cl, except that if A denotes phenylmethylsilyl then R" also denotes a methyl or a methoxy group.

2. A method of obtaining (E)-styryl-alkynylsubstituted silicon compound of formula 1:

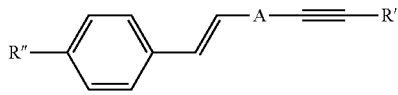
(1)

where:
   A denotes: phenylmethylsilyl, 1,4-bis(dimethylsilyl)benzene, 1,2-bis(dimethylsilyl)-ethane, 1,1,3,3-tetramethyldisilazane, or 1,1,3,3-tetramethyldisiloxane;
   R' denotes: tri(isopropyl)silyl, 1-pentyl, 2-(trimethylsiloxy)-2-butyl, 1-(trimethylsiloxy)-1-cyclohexyl, or triethylgermyl; and
   R" denotes: H or Cl, except that if A denotes phenylmethylsilyl then R" also denotes a methyl or a methoxy group,
   wherein the method consists of a silylative coupling reaction between a substituted styrene of formula 2;

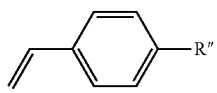
(2)

where R" denotes the same as stated above, and a vinyl-alkenyl-substituted silicon compound having the generalized of formula 3:

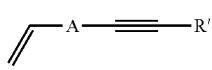
(3)

where A and R' denote the same as stated above, in the presence of a ruthenium(II) complex catalyst.

3. The method as claimed in claim 2, wherein the catalyst:
   [carbonylchlorohydridebis(tricyclohexylphosphine)ruthenium(II)],
   [carbonylchlorohydridebis(triphenylphosphine)ruthenium(II)], or
   [carbonylchlorohydridebis(triisopropylphosphine)ruthenium(II)].

4. The method as claimed in claim 3, wherein the catalyst is [carbonylchlorohydridebis(tricyclohexylphosphine)ruthenium(II)].

5. The method as claimed in claim 3, wherein the catalyst is used in an amount of 0.5-3.5 mol % relative to the vinyl-alkynyl-substituted silicon compound.

6. The method as claimed in claim 5, wherein the catalyst is used in the amount of 1-2 mol %.

7. A method of obtaining (E)-styryl-alkynylsubstituted silicon compound of formula 1:

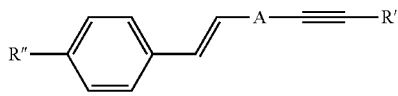
(1)

where:
   A denotes: phenylmethylsilyl, 1,4-bis(dimethylsilyl)benzene, 1,2-bis(dimethylsilyl)-ethane, 1,1,3,3-tetramethyldisilazane, or 1,1,3,3-tetramethyldisiloxane;
   R' denotes: tri(isopropyl)silyl, 1-pentyl, 2-(trimethylsiloxy)-2-butyl, 1-(trimethylsiloxy)-1-cyclohexyl, or triethylgermyl; and
   R" denotes: H or Cl, except that if A denotes phenylmethylsilyl then R" also denotes a methyl or a methoxy group:
   wherein the method consists of a sequence of two silylative coupling reactions of a terminal alkyene of formula 4:

(5)

where R' denotes the same as stated above with a divinyl-substituted silicon compound of formula 5:

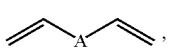
(5)

where A denotes the same as stated above, followed by a silylative coupling of the vinyl-alkynyl-substituted silicon compound produced in the first reaction with a substituted styrene of formula 2:

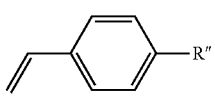
(2)

where R" denotes the same as stated above, in the presence of a ruthenium(II) complex catalyst.

8. The method as claimed in claim 7, wherein the catalyst used in the silylative coupling reaction of the terminal alkyene is:
   [carbonylchlorohydridebis(tricyclohexylphosphine)ruthenium(II)] or
   [carbonylchlorohydridebis(triisopropylphosphine)ruthenium(II)].

9. The method as claimed in claim 8, wherein the catalyst used is [carbonylchlorohydridebis(tricyclohexylphosphine)ruthenium(II)].

10. The method as claimed in claim 8, wherein the catalyst is used in an amount of 0.5-3.5 mol % relative to the vinyl-alkynyl-substituted silicon compound.

11. The method as claimed in claim 10, wherein the catalyst is used in the amount of 1-2 mol %.

12. A-The method as claimed in claim 7, wherein the catalyst used in the silylative coupling of the vinyl-alkynyl-substituted silicon compound, which is produced in the first reaction, with the substituted styrene of formula 2 is
   [carbonylchlorohydridebis(tricyclohexylphosphine)ruthenium(II)],
   [carbonylchlorohydridebis(triphenylphosphine)ruthenium(II)], or
   [carbonylchlorohydridebis(triisopropylphosphine)ruthenium(II)].

13. The method as claimed in claim 12, wherein the catalyst used is [carbonylchlorohydridebis(tricyclohexylphosphine)ruthenium(II)].

14. The method as claimed in claim 12, wherein the catalyst is used in an amount of 0.5-3.5 mol % relative to the vinyl-alkynyl-substituted silicon compound.

15. The method as claimed in claim 14, wherein the catalyst is used in the amount of 1-2 mol %.

16. The method as claimed in claim 4, wherein the catalyst is used in the an amount of 0.5-3.5 mol % relative to the vinyl-alkynyl-substituted silicon compound.

17. The method as claimed in claim 9, wherein the catalyst is used in an amount of 0.5-3.5 mol % relative to the vinyl-alkynyl-substituted silicon compound.

18. The method as claimed in claim 13, wherein the catalyst is used in an amount of 0.5-3.5 mol % relative to the vinyl-alkynyl-substituted silicon compound.

* * * * *